United States Patent [19]
Kaufhold et al.

[11] 4,117,251
[45] * Sep. 26, 1978

[54] METHOD FOR PREPARING STRAIGHT CHAIN PRIMARY ALCOHOLS FROM 1-BROMOALKANES

[75] Inventors: Manfred Kaufhold; Gottfried Bankwitz, both of Marl, Fed. Rep. of Germany

[73] Assignee: Chemische Werke Hüls AG, Marl, Fed. Rep. of Germany

[ * ] Notice: The portion of the term of this patent subsequent to Jul. 6, 1993, has been disclaimed.

[21] Appl. No.: 778,549

[22] Filed: Mar. 17, 1977

Related U.S. Application Data

[63] Continuation of Ser. No. 569,939, Apr. 21, 1975, abandoned.

[30] Foreign Application Priority Data

May 15, 1974 [DE] Fed. Rep. of Germany ....... 2423604

[51] Int. Cl.² .............................................. C07C 29/00
[52] U.S. Cl. ..................................... 568/877; 560/236
[58] Field of Search .................... 260/638 R; 560/236; 568/977

[56] References Cited

U.S. PATENT DOCUMENTS

| 1,459,971 | 6/1923 | Carter et al. | 560/236 |
| 3,655,701 | 4/1972 | Darre | 560/236 |
| 3,968,177 | 7/1976 | Kaufhold et al. | 260/638 R |

*Primary Examiner*—Joseph E. Evans
*Attorney, Agent, or Firm*—Gilbert L. Wells

[57] ABSTRACT

Straight-chain, primary alcohols are prepared by reacting straight-chain 1-bromoalkanes having 6 to 20 carbon atoms with alkali salts of monocarboxylic acids having 4 to 22 carbon atoms in the presence of 1 to 10 mole percent of monocarboxylic acids or alcohols based upon the alkali salt of the carboxylic acid and at temperatures ranging from 150° to 300° C. The esters formed are saponified in alkaline medium to the straight-chain, primary alcohols and separated.

8 Claims, No Drawings

METHOD FOR PREPARING STRAIGHT CHAIN PRIMARY ALCOHOLS FROM 1-BROMOALKANES

CROSS REFERENCES TO RELATED APPLICATIONS

The present application is a continuation of application Ser. No. 569,939 filed Apr. 21, 1975 and now abandoned.

Applicants claim priority under 35 U.S.C. 119 for Application P 24 23 604.2 filed May 15, 1974 in the Patent Office of the Federal Republic of Germany.

The disclosure of assignee's copending U.S. Application Ser. No. 505,044, filed Sept. 11, 1974, now U.S. Pat. No. 3,968,177 is incorporated herein. Application Ser. No. 505,044 discloses the state of the art of preparing straight-chain, primary alcohols by reacting straight-chain-1-chloroalkanes having 6 to 20 carbon atoms with alkali salts of monocarboxylic acids having 4 to 22 carbon atoms in the presence of 1 to 10 mole percent of monocarboxylic acids or alcohols based upon the alkali salt of the carboxylic acid and at temperatures ranging from 150° to 300° C.

BACKGROUND OF THE INVENTION

The field of the invention is straight-chain, primary alcohols.

Alcohols, especially primary, straight-chain alcohols are suitable basic materials for detergents, emulsifiers, lubricating oils etc. Further, primary, straight-chain alcohols may easily be converted, for instance by means of ethylene oxide, into ethoxylates that are easily biodegradable and furthermore, esterifications performed for instance with sulfur trioxide provide better yields than are obtained from branched alcohols.

The state of the art of preparing straight-chain, primary alcohols may be ascertained by reference to U.S. Pat. No. 3,401,206 of Horst-Dieter Wulf and Karl Geifert, which issued Sept. 10, 1968, and the Ullmann's Encyklopaedie der Technischen Chemie, 3rd Edition, Vol. 14 (1963), p. 612, and the Kirk-Othmer "Encyclopedia of Chemical Technology", 2nd Ed., Vol. 1 (1963), pp. 560–569, under the section Alcohols, Higher, Synthetic; Vol. 3 (1964), pp. 775–779 under the section Miscellaneous Bromine Compounds, Vol. 5 (1964), pp. 231–240, under the section Chlorinated Paraffins; and Vol. 8 (1966), pp. 356–361, under the section Ester Interchange, wherein alcoholysis in the presence of an alkaline catalyst is disclosed, the disclosures of which are incorporated herein.

Oxosynthesis is a process for preparing straight-chain, primary alcohols (see Ullmann's Encyklopaedie der Technischen Chemie, 3rd Ed., complementary volume, pp. 87–92). Oxosynthesis is always accompanied by an undesirable by-product in the form of the branched aldehyde, possibly following hydrogenation of the alcohol. The proportion of straight-chain compounds in the reaction mixture in all prior art processes employed so far has been less than 90 percent. Straight-chain, primary alcohols also are prepared by the so-called aluminum foil or Alfol process of K. Ziegler (see Ullmann's Encyklopaedie der Technischen Chemie, 3rd Ed., complementary volume, pp. 92–94, and Kirk-Othmer, ibid, Vol. 1, p. 560). Aluminum alkyls with higher unbranched alkyl groups are obtained, which may be transformed by air oxidation and subsequent hydrolysis of the aluminum alkoxides into a mixture of unbranched and straight-chain alcohols of various chain lengths. The drawback of this latter process is the great variation in length of the chains of the generated alcohols.

SUMMARY OF THE INVENTION

It is an object of the present invention to find a process for preparing primary, straight-chain alcohols with 6 to 20 carbon atoms, wherein the occurrence of isomeric by-products and of products of different chain lengths is avoided. The present invention achieves this objective by reacting primary, straight-chain 1-bromoalkanes having 6 to 20 carbon atoms with the alkali salts of monocarboxylic acids having 4 to 22 carbon atoms in the presence of 1-10 mole percent of monocarboxylic acids or alcohols, based on the alkali salt of the monocarboxylic acid and at temperatures of 150°–300° C., and by saponifying in alkaline medium according to the prior art, the esters so formed and separating the alcohols so occurring.

According to the process disclosed in Application Ser. No. 505,044, straight-chain primary alcohols are prepared by reacting straight-chain 1-chloroalkanes having 6–20 carbon atoms with the alkali salts of monocarboxylic acids having 4–22 carbon atoms in the presence of 1–10 mole percent of monocarboxylic acids or alcohols based on the amount of alkali salt of the carboxylic acid at temperatures from 150° to 300° C., the esters being formed being saponified in alkaline medium, and the alcohols so obtained being separated.

The present invention addresses the problem of further developing the process of Application Ser. No. 505,044 that other easily accessible or available basic materials may be used. The problem is solved by using 1-bromoalkanes in lieu of the 1-chloroalkanes.

Ester preparation takes place as in Application Ser. No. 505,044 by reacting an alkali salt of a carboxylic acid with 1-bromoalkanes, the rate of ester formation being favorably affected by even minute amounts of carboxylic acids or alcohols, as is the case for the above-mentioned patent application. From 1 to 10 mole percent of carboxylic acid or alcohol referred to the alkali salt of the monocarboxylic acid suffices. Preferably from 2 to 10 mole percent is used. Below 1 mole percent, the reaction rate drops excessively, while it is hardly affected above 10 mole percent. Only such alcohols are added which are to be prepared, or those that remain as residues during recovery. The most appropriate free acids used are those of which the alkali salts serve as ester components.

In order to obtain sufficiently high reaction rates for ester formation, the operating temperature exceeds 150° C., preferably falling within the range from 200° to 250° C. The ester yield above 300° C. drops because of increasing ester pyrolysis generating olefins and acids. Depending on temperature, the reaction is completed in about 2–4 hours.

DESCRIPTION OF THE PREFERRED EMBODIMENT

In conformity with the present invention, use is made of straight-chain 1-bromoalkanes with 6 to 20 carbon atoms. The temperatures required for ordinary reaction times (2–4 hours) cannot be achieved at standard pressure for straight-chain 1-bromoalkanes with fewer than 6 carbon atoms. Furthermore, the preparation of 100 percent straight-chain alcohols is easily feasible in this range of carbon atoms by means of oxosynthesis.

Straight-chain 1-bromoalkanes with more than 20 carbon atoms are difficult to handle industrially because of their high boiling points and the related easy decomposition in the boiling point range.

Carboxylic acids having 4–22 carbon atoms are used as the carboxylic acids or their alkali salts, preferably their sodium salts. Preferably sodium salts having 4–10 carbon atoms are used. When Na-acetate or Na-propionate with the addition of acetic acid or propionic acid are used as the ester components, only minor reactions are obtained. When carboxylic acids with more than 10 carbon atoms are used as ester components, then the alkaline saponification of the ester is accompanied by interfering foam-formation because of the higher fatty acids from the alkali salts formed. Those carboxylic acids are of especial favorable use of which the sodium salts are readily soluble in the reacting bromine compounds, for instance 2-ethylhexanoic acid. Salts from these acids are used as non-aqueous solutions in organic solvents or reaction products for ester-formation, and precipitate as such again following alkaline saponification. Furthermore, being solutions that are easily pumped, they can be readily handled.

Saponification of the esters prepared pursuant to the present invention takes place in conventional manner, generally by adding aqueous solutions of an alkali or alkali earth metal hydroxide, preferably sodium hydroxide. After saponification, a substance is added to the mixture, this substance being of a boiling point higher than that of the generated alcohol, which may be easily distilled off later, for instance the residue from an oxo-alcohol or a residue precipitating in the Alfol process. Thereupon distillation immediately takes place, the converted water being separated as first run. After the alcohol has been distilled off, one obtains the solution of the alkali salt from the carboxylic acid used in the high boiling point residue of the oxo-alcohol or Alfol in the sump. This salt solution may again be used for ester formation. One may also, for instance, dilute the reaction mixture by means of an organic solvent, for instance cyclohexane, wash it with water and then recover the organic phase by distillation. The desired alcohols are obtained from the distillation. As regards this procedure, the alkali salts of the carboxylic acids again are precipitated as an aqueous solution and as such may also be applied for ester formation.

The process of the present invention in this manner allows preparing straight chain primary alcohols from 1-bromoalkanes with very good yields.

Any 2-bromoalkanes present as contaminations will not react into esters in the process of the present invention, rather they will supply olefins which may be easily separated from the generated esters. As was observed, very pure alcohols are obtained after saponification of the separated esters for the reasons cited.

Preparation of 1-bromoalkanes may take place in conventional manner by juxtaposing hydrobromic acid to α-olefins in the presence of peroxides or ultra-violet light (as radical forming agents), by dissociating ethers by means of hydrobromic acids, by decomposing carboxylic acids or their salts, as disclosed in Kirk-Othmer ibid, and Ullmann's, ibid.

For example, straight chain 1-bromoalkanes may be prepared by hydrobrominating alpha olefins having 6 to 20 carbon atoms in the presence of UV light or peroxides and fractionally distilling said brominated alpha olefins to remove olefins generated by said bromination, non-reacted alpha olefins and unidentified impurities and separating said straight chain 1-bromoalkanes as a sump product.

The process of the invention therefore allows preparing straight chain primary alcohols, for instance starting from α-olefins and by means of 1-bromoalkanes and esters.

Specific examples of the 1-bromoalkanes having 6–20 carbon atoms and useful in the present invention have a bromine content of about 22 to 48 percent and include, but are not limited to:

1-bromohexane, 1-bromoheptane, 1 bromooctane, 1 bromononane, 1 bromodecane, 1-bromoundecane, 1-bromododecane, 1-bromotridecane, 1-bromotetradecane, 1-bromopentadecane, 1-bromohexadecane, 1-bromoheptadecane, 1-bromooctadecane, 1-bromononadecane, and 1-bromoeicosane.

Specific examples of the alkali salts of monocarboxylic acids having 4–22 carbon atoms and useful in the present invention include, but are not limited to: sodium salt of 2-ethylhexanoic acid, sodium salt of caprylic acid, sodium salt of behenic acid, sodium salt of isobutyric acid, sodium salt of n-butyric acid, sodium salt of i-valeric acid, sodium salt of n-valeric acid, sodium salt of i-capronic acid, sodium salt of n-capronic acid, sodium salt of i-oenanthic acid, sodium salt of n-oenanthic acid, sodium salt of i-caprylic acid, sodium salt of i-pelargonic acid, sodium salt of n-pelargonic acid, sodium salt of i-capric acid, sodium salt of n-capric acid, sodium salt of i-undecanioc acid, sodium salt of n-decanoic acid, sodium salt of tauric acid, sodium salt of a branched chain C12 acid, sodium salt of n-tridecanoic acid, sodium salt of a branched chain C13 acid, sodium salt of myristic acid, sodium salt of a branched chain C14 acid, sodium salt of daturic acid, sodium salt of a branched chain C15 acid, sodium salt of palmitic acid, sodium salt of a branched chain C16 acid, sodium salts of straight or branched chain heptadecanoic acids, sodium salt of stearic acid, sodium salt of a branched chain C18 acid, sodium salt of straight or branched chain nonedecanoic acid, sodium salt of arachic acid, sodium salt of branched chain C20 acid, sodium salt of behenic acid, sodium salt of branched chain C22 acid. Instead of these sodium salts may also be used, e.g., the potassium, magnesium, calcium or barium salts.

Specific examples of the monocarboxylic acids useful in the present invention and having 4 to 22 carbon atoms include, but are not limited to: 2-ethylhexanoic acid, caprylic acid, n- and i-butyric acid, n- and i-valeric acid, n- and i-capronic acid, n- and i-oenanthic acid, i-caprylic acid, n-caprylic acid, n- and i-pelargonic acid, n- and i-capric acid, n- and i-undecanoic acid, n- and i-dodecanoic acid, n- and i-tridecanoic acid, myristic acid, branched chain C14 acid, daturic acid, branched chain C15 acid, palmitic acid, branched chain C16 acid, straight chain and branched chain C17 acid, stearic acid, branched chain C18 acid, straight chain and branched chain C19 acid, arachic acid, branched chain C20 acid, straight and branched chain C21 acid, behenic acid and branched chain C22 acid. If the free acid is not identical with the acid of the sodium salt, a mixture of esters of the different acids is formed. If the boiling points of the formed esters are too different this may cause difficulties in the distillation step.

Specific examples of the alcohols useful in the present invention and having 6 to 20 carbon atoms include, but are not limited to: tallow fat alcohol, straight and branched chain C6 alcohols, straight and branched chain C7 alcohols, straight and branched chain octanols, straight and branched chain nonanols, straight and branched chain decanols, straight and branched chain undecanols, straight and branched chain dodecanols, straight and branched chain C13 alcohols, straight and branched chain C14 alcohols, straight and branched chain C15 alcohols, straight and branched chain C16 alcohols, straight and branched chain C17 alcohols, straight and branched C18 alcohols, straight and branched chain C19 alcohols, straight and branched chain C20 alcohols. Preferably those alcohols are used which allow, because of their high boiling point, the use of high temperatures without pressure during the esterification reaction and which can be separated by distillation from the formed main- and by-product.

The esterification reaction of the present invention is carried out at a temperature of about 150°-300° C., preferably 200°-250° C., for a period of about 10 minutes to 5 hours, preferably 1 to 2 hours.

The examples listed below serve to further explain the present invention.

EXAMPLE 1

486 gm (2.77 moles) of 1-bromohexane (94%) and 471 gm (2.80 moles) of sodium salt of the 2-ethylhexanoic acid (98.8%) and 9 gm of 2-ethylhexanoic acid are heated with stirring for 5 hours to 190° C. (While heating, an exothermal reaction sets in beyond 150° C.). Following cooling, the sodium bromide formed is disssolved by means of 640 gm of water and provides an aqueous solution of 855 gm.

The organic phase (731 gm) has an acid number of 11.21 and is neutralized by means of 22 gm of 25 percent sodium hydroxide. The waste water (102 gm) is discarded.

The reaction product is distilled in a 0.5 m long column filled with glass Raschig rings at 10 torr (torr = 1 mm Hg) (reflux ratio = $\frac{1}{3}$). 23 gm of first run are obtained in a boiling point range from 50 to 131° C. and 592 gm of pure ester with a saponification number of 255.1 are obtained in a range from 131° to 133° C.

The residue amounts to 10 gm. Yield is 93.7 percent of theoretical.

Saponification of the ester is performed conventionally and provides pure 1-hexanol.

EXAMPLE 2

548 gm (2.2 moles) of 1-bromododecane are mixed with 405 gm (2.4 moles) of sodium salt of the 2-ethylhexanoic acid (98.4%) with an acid number of 5.55 and with 5 gm of 2-ethylhexanoic acid and the mixture is heated for 2 hours at 200° C. Following cooling, the sodium bromide formed is dissolved by means of 500 gm of water, providing an aqueous solution of 748 gm.

The acid number of the organic phase (700 gm) is 7.58 and is neutralized by means of 15 gm of 25 percent sodium hydroxide. The waste water is discarded.

The reaction product is distilled in a 0.5 m long column filled with glass Raschig rings at 10 torr (reflux ratio = $\frac{1}{3}$). 16 gm of first run are obtained in a boiling point range from 130° to 193° C., and 639 gm of pure ester in a range from 193° to 203° C. Only 5 gm of residue remain. Yield is 93.2 percent of theoretical.

Ester saponification is performed conventionally and produces pure 1-dodecanol.

EXAMPLE 3

C-18 and C-20 bromoalkanes react in the same manner with the corresponding ester.

We claim:

1. In a process for preparing straight-chain, primary alcohols having 6–20 carbon atoms, the improvement comprising reacting at a temperature of about 150° to 300° C. straight-chain 1-bromoalkanes having 6 to 20 carbon atoms with alkali salts of alkanoic acids having 4 to 22 carbon atoms in the presence of 1 to 10 mole percent of alkanoic acids having 4 to 22 carbon atoms based on said alkali salts of the alkanoic acids to form esters, saponifying said esters in an alkaline medium to form straight-chain, primary alcohols having 6–20 carbon atoms and separating said straight-chain, primary alcohols.

2. The process of claim 1, wherein said alkali salts of alkanoic acids have 4 to 10 carbon atoms.

3. The process of claim 2, wherein said reacting temperature is about 200° to 250° C.

4. A process for preparing straight-chain, primary alcohols having 6–20 carbon atoms, comprising:
   (a) hydrobrominating α olefins having 6 to 20 carbon atoms in the presence of UV light or peroxides to form brominated α olefins;
   (b) fractionally distilling said brominated α olefins;
   (c) separating straight-chain 1-bromoalkanes having 6 to 20 carbon atoms as sump product;
   (d) reacting said straight-chain 1-bromoalkanes with alkali salts of alkanoic acids having 4 to 22 carbon atoms in the presence of 1 to 10 mole percent of alkanoic acids having 4 to 22 carbon atoms and at a temperature of about 150° to 300° C. to form esters;
   (e) saponifying said esters in an alkaline medium to form said straight-chain, primary alcohols having 6–20 carbon atoms; and
   (f) separating said straight chain, primary alcohols.

5. The process of claim 4, wherein step (d) is carried out at a temperature of about 200° to 250° C.

6. The process of claim 4, wherein step (d) is carried out for a period of about 10 minutes to 5 hours.

7. The process of claim 4, wherein step (d) is carried out for a period of about 1 to 2 hours.

8. The process of claim 4, wherein said 1-bromoalkanes have a bromine content of about 22 to 46 percent and are selected from the group consisting of 1-bromohexane 1-bromoheptane, 1-bromooctane, 1-bromononane, 1-bromodecane, 1-bromoundecane, 1-bromododecane, 1-bromotridecane, 1-bromotetradecane, 1-bromopentadecane, 1-hexadecane, 1-bromoheptadecane, 1-bromooctadecane, 1-bromononadecane, 1-bromoeicosane and mixtures thereof.

* * * * *